June 5, 1973 C. PEARLSTEIN Plant Pat. 3,352
AZALEA PLANT
Filed May 4, 1970
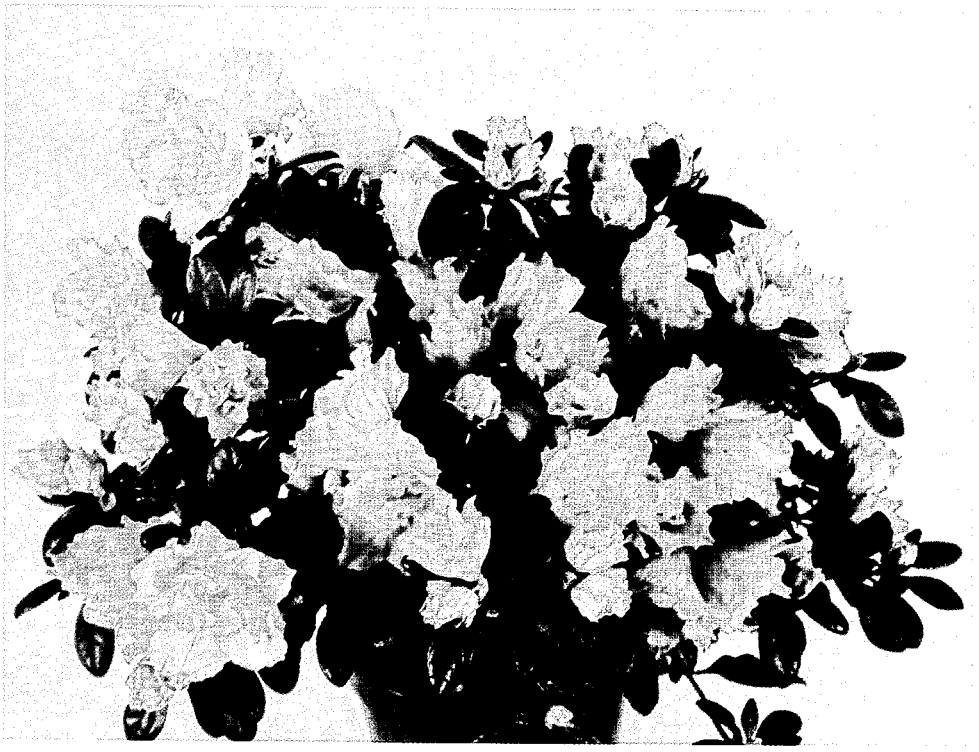

United States Patent Office

Plant Pat. 3,352

Patented June 5, 1973

3,352

AZALEA PLANT

Carl Pearlstein, San Francisco, Calif., assignor to Nurserymen's Exchange, Inc.

Filed May 4, 1970, Ser. No. 34,644

Int. Cl. A01h *5/00*

U.S. Cl. Plt.—57 1 Claim

The invention relates to a new and distinct variety of azalea plant of the Belgian Indica class, discovered by me in a cultivated area, namely in the greenhouses of Nurserymen's Exchange at Half Moon Bay, Calif. My new azalea plant is a sport of "Improved Red Wing," Plant Patent 2,918.

This sport was selected and propagated because of its novel color, i.e. the color of its blossoms is of a lighter hue. This characteristic in combination with the superior vegetative characteristics of the parent make this variety novel and superior to other Belgian Indica varieties in its color class. This color characteristic which is outstanding in the new variety distinguish it from its parent as well as from all other varieties of which I am aware.

My new variety is primarily characterized by: its vegetative similarity to "Improved Red Wing," above identified, of which it is a sport, by its fast and vigorous growth and by its Phlox Pink (H.C.C. 625/1).

Asexual reproduction of my new variety by cuttings, through a series of propagations at the greenhouses of Nurserymen's Exchange at Half Moon Bay, Calif., shows that all characteristics of the variety come true to form through succeeding propagations. The accompanying photograph illustrates the primary characteristics of my new variety as nearly true as is reasonably possible to make them with presently available techniques. The color reference cited is that of the Horticultural Colour Charts of the Royal Horticultural Society.

The following botanical description is based upon observations of plants in clay pots grown under greenhouse conditions at Half Moon Bay, Calif.

A new variety of Florists Azalea of the Belgian Indica class characterized by its vegetative similarity to "Improved Red Wing" of which it is a somatic mutation, but differing from the parent variety in color. Large, robust ascending plant spreading 40–48 inches high and 30–36 inches across at maturity. Branches stout, but supple, gently arching. Basal shoots vigorous, about ⅛ inch in diameter, axillary branches about 3/32 inch the first season. Internodes of basal shoots between ⅛ inch and ⅝ inch long. Stems eret to slightly pendulous; rufous when young, becoming light green at the base and becoming rufous to brown when old. Bark more or less conspicuously striate, young stems bearing prominent hyaline to chestnut striga (becoming chestnut with age, i.e. located on basal portion of stem).

Foliage evergreen, of two size classes. Leaves of vigorous growth about 1½ to 1⅞ inches long between ¾ to 1⅛ inches wide, petiolate, the petioles about 5/16 inch long, lamina decurrent, descending the petiole up to ⅛", elliptic. The margin is entire, somewhat ciliate, the cilia small, inconspicuous. The apex is acute. The midrib is pubescent, especially below. The trichomes are flat, lanceolate, slender up to 3/32" in length, conspicuous, hyaline, abundant on the lower surface, smaller, sparser, and hyaline on the upper surface of the midrib. The lamina is sparsely pubescent above and somewhat heavier below. Leaves of the branches from the older wood smaller, about ¾–1⅛" long by ⅜–½" wide with proportionally smaller trichomes, but otherwise similar to the larger leaves. The color of the leaves is Spinach Green (H.C.C. 0960) 26 above and Spinach Green (H.C.C. 0960/2) below.

The bud of the inflorescence is Pod Green (H.C.C. 061) The scales are small, about ¼" wide by about ½" long, heart shaped to strap shaped becoming cucullate at anthesis. Pubescence is moderate to heavy, small, golden brown essentially restricted to the rib. The scales become scarious with sub-hyaline margins at dehiscence.

The inflorescence is 2–3 flowered. The flowers are borne in an umbellate corymb. One flower of the three-flowered inflorescences matures several days later than the more precocious pair and has a shorter peduncle. The peduncles are short, stout 7/16–⅝" long by 3/32" wide, pubescent, light green to red (where exposed to sunlight). Pubescence moderately dense, hyaline to chestnut, where exposed to sunlight, wtih pink bases, short and silky. Calyx corolliform, sepals imperfect, ragged, 5 lobed. Tube of calyx about ¾" deep by ¾" across, broadly flared, lightly fluted, very irregular and fimbriate. Lobes from ¼–¾" wide by ¾–1¼" long or some lobes entirely missing; highly variable as to shape and size, secondarily lobed and incised. The margins of the lobes are long ciliate. The reverse of the calyx is splotched with Rose Madder (H.C.C. 23) and is sparsely pubescent. Located between the calyx and corolla are from 1–4 corolline appendages from ¾–½" long. The corolla is Phlox Pink (H.C.C. 625/1) with freckles of Rose Madder (H.C.C. 23) on the tube of the standard.

The reverse is Phlox Pink, H.C.C. 625/1) on the corolla lobes and tube. The calyx and appendages are the same color as the corolla. The tube is about 1⅛" long by 13/16" across at the throat, flaring bilaterally symmetrical, slightly gibrous, somewhat higher than broads, more or less prominently fluted. The five corolla lobes are of two size classes, the ventral two larger about 1⅛"–1⅜" across by 1¼"–1½" long undulate. The dorsal 3 lobes are smaller, about 1⅛"–1¼" across by ⅞"–1" long. The flower is about 3–3½" across by 2–2¼" deep.

The Stamens are five, filaments slender, Rose Madder (H.C.C. 23/1), ¾"–1¾" long, the staminodia are petaloid and are 4–5 in number. They come in two sizes; the larger 2 measure about ½" wide and 2–2⅛" long, the smaller 2–3, measure about 3/16" wide by ⅝–¾" long. Anthers small, black, about 1/16" by 3/32", pollen white. The pistil is long, 1¼–1½" long, stigma Rose pink, capitate, 5 lobed, receptive surface divided into 5 sections; style slender, 1¼" long (about), curved not sigmoid, not expanded at base. Ovary about 5/32" long by ⅛" across, heavily pubescent, the pubescence dense, long, silky, hyaline.

Having thus disclosed my invention, I claim:

1. A new and distinct variety of azalea plant of the Belgian Indica class substantially as herein shown and described primarily characterized by: its vegetative similarity to "Improved Red Wing" of which it is a sport and by its Phlox Pink (H.C.C. 625/1).

No references cited.

ROBERT E. BAGWILL, Primary Examiner